US00PP21529P3

(12) United States Plant Patent
Kordes

(10) Patent No.: US PP21,529 P3
(45) Date of Patent: Nov. 30, 2010

(54) SHRUB ROSE PLANT NAMED 'KORPAROFE'

(50) Latin Name: *Rosa hybrida*
Varietal Denomination: KORparofe

(75) Inventor: Tim-Hermann Kordes, Klein Offenseth-Sparrieshoop (DE)

(73) Assignee: W. Kordes' Söhne Rosenschulen GmbH & Co KG, Offenseth-Sparriashoop (DE)

( * ) Notice: Subject to any disclaimer, the term of this patent is extended or adjusted under 35 U.S.C. 154(b) by 0 days.

(21) Appl. No.: 12/283,515

(22) Filed: Sep. 12, 2008

(65) Prior Publication Data

US 2009/0038035 P1 Feb. 5, 2009

(51) Int. Cl.
*A01H 5/00* (2006.01)

(52) U.S. Cl. ..... Plt./107

(58) Field of Classification Search ..... Plt./107
See application file for complete search history.

(56) References Cited

OTHER PUBLICATIONS

GTITM UPOVROM Citation for 'Korparofe' as per QZ PBR 20070818; Apr. 10, 2007.*

2007/0818 European Union CVPO summary Apr. 15, 2007 European Union.

2007/0818 European Union CVPO summary Jun. 15, 2007 European Union.

Photostatic copy of the index page of W. Kordes Sohne 2007/2008 catalog demonstrating that 'Zaide', the commercial name for 'KORparofe' was not listed.

Photostatic copy of the index page of W. Kordes Sohne 2008/2009 catalog demonstrating that 'Zaide', the commercial name for 'KORparofe' was first listed.

Photostatic copy of p. 34 of W. Kordes Sohne 2008/2009 catalog demonstrating that plant material of 'Zaide' was listed as 'New' at this time.

A printout of the webpage of W. Kordes Sohne demonstrating that 'Zaide', the commercial name for 'KORparofe', was listed as 'New' in 2008.

* cited by examiner

*Primary Examiner*—Kent L Bell

(57) ABSTRACT

A new and distinct variety of rose with long lasting, novel pink flowers, and attractive foliage with good disease resistance. It exhibits bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORparofe'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 1994. The crossing was between 'DELge' and 'KORtuge'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORparofe'.

SUMMARY OF THE INVENTION

The new rose plant may be distinguished from its seed parent, 'DELge', by the following combination of characteristics:

1. The foliage size of 'DELge' is medium, while the foliage size of 'KORparofe' is large.
2. The petal count of 'DELge' is semi-double, while the petal count of 'KORparofe' is very double.

The new rose plant may be distinguished from its pollen parent, 'KORtuge' by the following combination of characteristics:

1. The flower bloom of 'KORtuge' is yellow, while the flower bloom of 'KORparofe' is pink.
2. The fragrance of 'KORtuge' is slight, while the fragrance of 'KORparofe' is strong.

The objective of the hybridization was to create a new and distinct rose plant with unique qualities, such as:

1. Compact and uniform growth and flowering; when grown as a plant from cuttings;
2. Abundant attractive, recurrent flowers;
3. Attractive and abundant foliage; and
3. Resistance to diseases encountered in landscapes and gardens.

This combination of qualities is not present in prior rose cultivars. These objectives have been substantially achieved and in that distinguish 'KORparofe' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORparofe' was selected in May, 1994 from the seedling beds to be asexually propagated for further evaluation. The first asexual propagation of 'KORparofe' was done by budding to seedling understocks in July, 1995 at the inventor's nursery in Offenseth-Sparrieshoop, Germany.

This initial and other subsequent propagations conducted in controlled environments demonstrate that 'KORparofe' reproduces true to type in successive generations of asexual reproduction.

BRIEF DESCRIPTION OF THE DRAWING

The accompanying color illustration shows as true as is reasonably possible to obtain in color photographs of this type, the typical characteristics of the buds, flowers, leaves, and stems of 'KORparofe'. Specifically illustrated in SHEET ONE is a stem exhibiting thorns; tight bud and open flower bloom; juvenile foliage and tip of stem; dissected receptacle and detached sepal; hip; and leaves.

DETAILED BOTANICAL DESCRIPTION

The following is a description of 'KORparofe', as observed in its growth in October, 2007 in a nursery in Jackson County, Oreg. on plants of three years of age. Color references are made using The Royal Horticultural Society (London, England) Colour Chart, 2001 except where common terms of color are used.

For a comparison, several physical characteristics of the rose variety 'KORpriggos', a rose variety from the same inventor described and illustrated in U.S. Plant patent application Ser. No. 11/893,516 and filed on Aug. 15, 2007 are compared to 'KORparofe' in Chart 1.

CHART 1

| Characteristic | 'KORparofe' | 'KORpriggos' |
|---|---|---|
| Flower color, ¼ open | Upper surface: Red-Purple Group 63D. Lower surface: Red-Purple Group 63C (marginal zone), Red-Purple Group 63B (middle zone), and Red-Purple Group 63A (basal zone). | Upper surface: Orange-White Group 159D. Lower surface, marginal zone: White Group 155D. Transitions to a large marginal zone of Yellow Group 2D. |
| Petal Count | Flower is very double, with 90-110 petals on average | Flower is double to very double, with 45-50 petals on average |

Parents:

*Seed parent.*—'DELge'.

*Pollen parent.*—'KORtuge'.

Classification:

*Botanical classification.*—*Rosa hybrida,* 'KORparofe'.

*Commercial classification.*—Shrub rose.

FLOWER AND FLOWER BUD

Blooming habit: Recurrent.

*Flower bud.*—Size: Upon opening, 40-45 mm in length from base of receptacle to end of bud and 25 mm in diameter at its widest point. Bud form: Short and pointed ovoid. Bud color: As sepals first unfold, bud color is Red-Purple Group 61A and Red-Purple Group 61B. When ¼ open, the upper surface of petals is Red-Purple Group 63D. The lower surface is Red-Purple Group 63C (marginal zone), Red-Purple Group 63B (middle zone), and Red-Purple Group 63A (basal zone).

*Sepals.*—Size: Average 20 mm long×9 mm wide. Shape: Sepals generally subulate. Sepal apex is generally cirrose. Weak foliaceous appendages on three of the five sepals. Base is flat at union with receptacle. Quantity: Five. Margins: With moderate numbers of stipitate glands present. Surface texture: Inner side: Covered in wooly, white hairs. Outer surface: Smooth. Color: Upper surface Yellow-Green Group 144C. Lower surface Green Group 143A. Intonations: Greyed-Purple Group 184B.

*Receptacle.*—Surface: Smooth. Color: Yellow-Green Group 144B. Shape: Funnel-shaped. Size: 11-12 mm (h)×13 mm (w).

*Peduncle.*—Surface: With stipitate glands. Length: 40-45 mm average length. Diameter: 3-4 mm average diameter. Color: Yellow-Green Group 145A. Strength: Strong. Borne: Multiple flower buds per stem, generally 5 to 6. Anthocyanin: Greyed-Purple Group 184A.

Flower bloom:

*Fragrance.*—Strong.

*Duration.*—Long lasting. The blooms have a duration on the plant of approximately 6 to 8 days. Senesced petals drop away cleanly. The duration of a cut bloom is 4 to 6 days.

*Size.*—Large flowered garden rose. When open, the average flower diameter is 100 mm and the average flower height is 55 mm.

*Form.*—Shape of flower when viewed from the side: Upon opening, upper part: Flat. Upon opening, lower part: Flat. Open flower, upper part: Flattened Convex. Open flower, lower part: Concave.

Color:

*Upon opening, petals.*—Outermost petals: Outer Side: Red-Purple Group 68B and Red-Purple Group 68C. Intonations of Red-Purple Group 61C. Inner Side: Red-Purple Group 69A. Innermost petals: Outer Side: Red-Purple Group 63A. Inner Side: Red-Purple Group 52B.

*Upon opening, basal petal spots.*—Basal petal spot, outermost petals: Outer Side: Green-Yellow Group 1C. Inner Side: Green-Yellow Group 1B. Basal petal spot, innermost petals: Outer Side: Green-Yellow Group 1B. Inner Side: Green-Yellow Group 1A.

*After opening, petals.*—Outermost petals: Outer Side: Red-Purple Group 65B and Red-Purple Group 65C. Inner Side: Red-Purple Group 70D. Innermost petals: Outer Side: Red-Purple Group 65A. Inner Side: Red-Purple Group 68B.

*After opening, basal petal spots.*—Basal petal spot, outermost petals: Outer Side: Green-Yellow Group 1D. Inner Side: Green-Yellow Group 1D. Basal petal spot, innermost petals: Outer Side: Green-Yellow Group 1C. Inner Side: Green-Yellow Group 1C.

General tonality: On open flower Red-Purple Group 65A and Red-Purple Group 65B. No change in the general tonality.

Petals:

*Petal count.*—Approximately 90-100 petals under normal conditions.

*Petal reflex.*—Petals reflex strongly.

*Petal edge.*—Entire, with limited undulations.

*Petal shape.*—Obovate. Apex shape is round. Shape of base is acute.

*Petal size.*—45-50 mm long; 35-40 mm wide.

*Thickness.*—Average.

*Petal arrangement.*—Generally in a regular pattern with overlapping edges.

Petaloids: Present.

*Petaloid count.*—Average of 20-30 per flower.

*Petaloid edge.*—Undulated.

*Petaloid texture.*—Ruffled.

*Petaloid shape.*—Elongated. Entire. Shape of apex is round, shape of base is pointed.

*Petaloid size.*—Petaloids are 10 mm long and 6 mm wide.

*Petaloid color.*—Color of inner side is Red-Purple Group 63B with intonations of Red-Purple Group 63A. Color of outer side is Red-Purple Group 63B.

Reproductive organs:

*Pistils.*—Approximately 50-60 present. Stigmas: Location: Slightly superior in position to anthers. Color: Yellow Group 2B. Styles: Length: 8-9 mm long. Color: Red-Purple Group 58A. Intonations of Green-Yellow Group 1C.

*Stamens.*—Approximately 10-20 on average and regularly arranged. Anthers: Size: 1.5-2.0 mm long. Color: Yellow-Orange Group 16A and Yellow-Orange Group 16C. Pollen: Absent. Filaments: Color: Red-Purple Group 62D with intonations of Red-Purple Group 62C. Length: 7-8 mm.

THE PLANT

*Plant growth.*—Vigorous. Bushy habit. When grown as a budded nursery plant the average plant height is 160-200 cm and the average plant width is 100-130 cm.

*Stems.*—Stem color: Young wood: Yellow-Green Group 145A. Older wood: Yellow-Green Group 144A. Stem surface: Young wood: Smooth. Older wood: Smooth.

*Prickles.*—Present. Incidence: 8-12 per 10 cm of stem. Size: Average length: 9 mm. Color: Immature prickles: Greyed-Yellow Group 161A. Mature prickles: Greyed-Orange Group 165B. Senescing to Greyed-Orange Group 166A. Shape: Concave. Anthocyanin: Greyed-Purple Group 184B and Greyed-Purple Group 185C.

*Leaves and leaflets.*—Normally 5-7 leaflets on normal leaves in middle of the stem. Venation pattern: Pyramidal net pattern. Leaf size: 130 mm (l)×100 mm (w). Quantity: Limited. Texture: Upper side of leaflet: Semi-glossy and smooth. Under side of leaflet: Matte and rough. Color, mature foliage: Upper Leaf Surface: Green Group 137A. Lower Leaf Surface: Green Group 138B. Color, juvenile foliage: Upper Leaf Surface: Green Group 138A. Lower Leaf Surface: Green Group 138B. Anthocyanin intonation: Greyed-Purple Group 183A.

*Stipules.*—Size: 20 mm long. 7 mm between the tips of the stipule. Main body of stipule 6 mm in width. Shape: Longitudinally flanged or winged along middle. Stipule color: Green Group 143A. Presence of stipitate glands: Present on margins. Margins: Serrated. With stipitate glands.

*Petiole.*—Length: 4-5 mm. Diameter: 1.5-2.0 mm. Petiole color: Green Group 143A. Underneath: Smooth. Stipitate glands: Present on margins.

*Petiole rachis.*—Length: 16 mm. Diameter: 1.5 mm. Color: Green Group 143B. Margins: With stipitate glands. Prickles: Not observed. Anthocyanin: Greyed-Purple Group 183A.

*Leaflets.*—Size: Average size of the terminal leaflet is 60 mm (l)×35 mm(w). Shape: Ovate. Base: Ovate. Apex: Acute. Margins: Serrated. Texture: Thick and leathery.

Hips/seed formation: Present.

*Size.*—30 (h)×22 (w).

*Color.*—Yellow-Green Group 146C with intonations of Orange Group 25A.

Winter hardiness: To date, the variety has been grown successfully in Zone 5.

Disease resistance: Above average resistance to powdery mildew, rust, and Black spot disease under normal growing conditions.

I claim:

1. A new and distinct variety of rose plant characterized by the following combination of characteristics:

(a) Forms attractive, long lasting pink flowers;

(b) Exhibits bushy growth habit;

(c) Propagates well using traditional methods, and;

(d) Exhibits very good resistance to disease under normal growing conditions, substantially as herein illustrated and described.

* * * * *

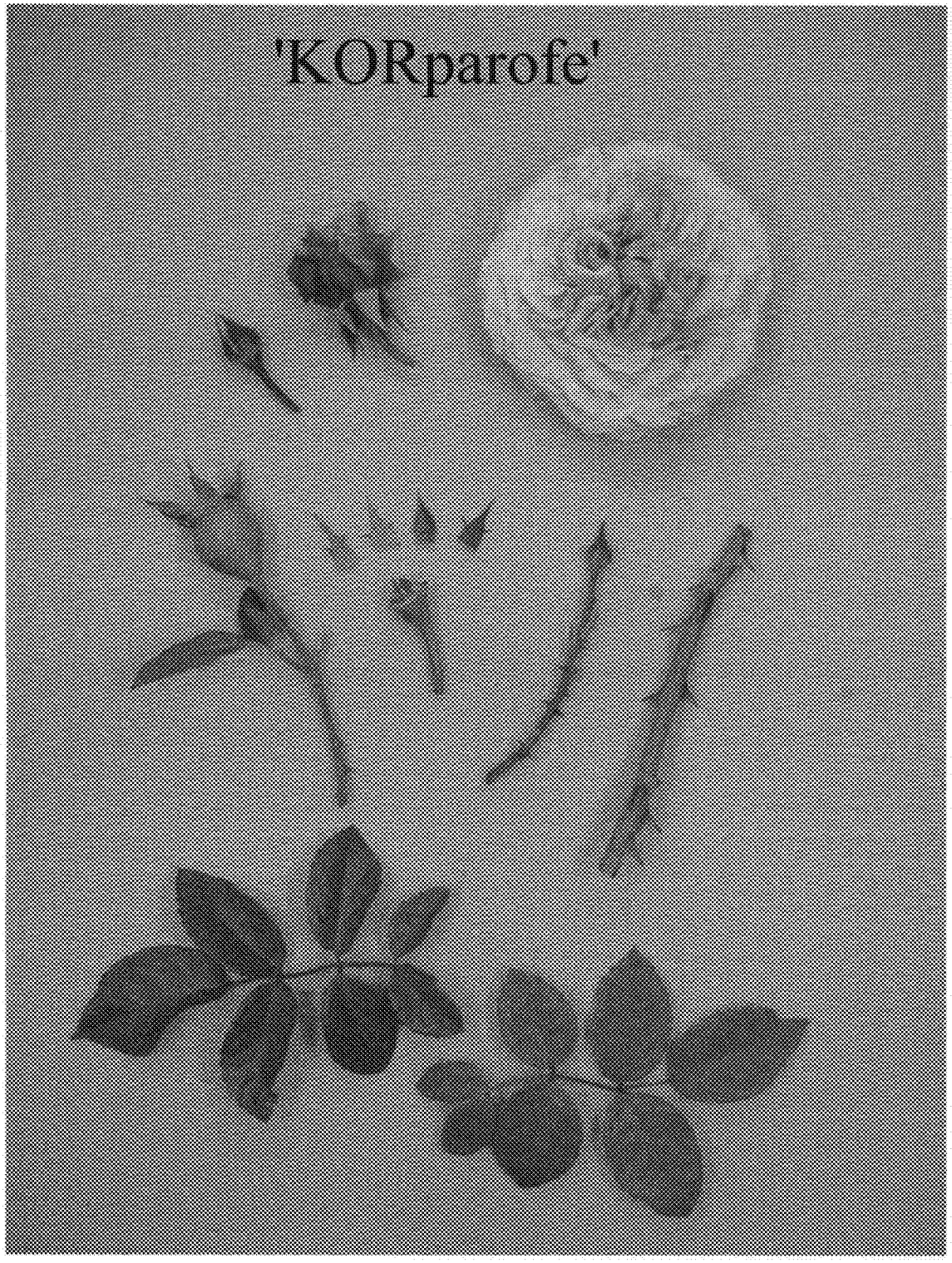
'KORparofe'